United States Patent [19]

Holliday et al.

[11] Patent Number: 4,978,345

[45] Date of Patent: Dec. 18, 1990

[54] REUSABLE MULTI-LAYERED DIAPER

[76] Inventors: Craig S. Holliday; Deborah A. Holliday, both of 3990 Washington Way, Morrow, Ohio 45152

[21] Appl. No.: 399,726

[22] Filed: Aug. 28, 1989

[51] Int. Cl.5 .............................................. A61F 13/15
[52] U.S. Cl. .................................. 604/384; 604/377; 604/378
[58] Field of Search ........................ 604/377, 378, 384

[56] References Cited

U.S. PATENT DOCUMENTS

| | | | |
|---|---|---|---|
| 342,494 | 5/1886 | Baldwin | 604/378 |
| 580,406 | 4/1897 | Kleinert | 604/386 |
| 2,097,903 | 11/1937 | Wallis | 604/373 |
| 2,256,510 | 9/1941 | Young | 128/284 |
| 2,515,737 | 7/1950 | Schwarzberger | 128/287 |
| 2,558,215 | 6/1951 | Habig et al. | 128/287 |
| 2,833,282 | 4/1958 | Moore | 128/284 |
| 3,063,452 | 11/1962 | Guercio | 128/284 |
| 3,072,123 | 1/1963 | Davis | 128/284 |
| 3,498,296 | 3/1970 | Gallagher | 128/284 |
| 3,530,859 | 9/1970 | Heimowitz | 128/284 |
| 3,699,966 | 10/1972 | Chapuis | 604/377 |
| 3,719,189 | 3/1973 | Sherman | 128/287 |
| 3,838,693 | 10/1974 | Sherman | 128/287 |
| 3,842,837 | 10/1974 | Sward | 604/377 |
| 4,102,340 | 7/1978 | Mesek et al. | 604/377 |
| 4,128,686 | 12/1978 | Kyle et al. | 604/391 |
| 4,196,733 | 4/1980 | Elias-Geisseler | 128/287 |
| 4,282,874 | 8/1981 | Mesek | 604/365 |
| 4,573,987 | 3/1986 | Lamb, Jr. | 604/378 |
| 4,813,946 | 3/1989 | Sabee | 604/385.2 |
| 4,850,987 | 7/1989 | Gilomen | 604/377 |

Primary Examiner—Randall L. Green
Assistant Examiner—Gary Jackson
Attorney, Agent, or Firm—Mark F. Smith

[57] ABSTRACT

A multi-layer, reusable, washable diaper for infants having a substantially 100% cotton facing sheet for contacting the skin of the infant, at least one sheet of absorbing fibrous batt material for drawing and retaining moisture away from the skin of the infant, a flexible liquid impermeable material backing sheet, and a decorative outer cover. The sheets are stitched together using a quilting pattern to generally immobilize the fibers of the batt material sheets to maintain their position and thickness after repeated washing and drying cycles. The diaper is fastened in place on the infant by non-metallic fastening devices which fasten together on the backside of the diaper and out of sight and easy reach of the infant.

3 Claims, 4 Drawing Sheets

REUSABLE MULTI-LAYERED DIAPER

BACKGROUND OF THE INVENTION

The present invention relates to reusable multi-layered absorbent diapers for use in collecting wastes such as urine and fecal matter until the diaper is changed.

The large use of synthetic disposable products such as diapers for infants has received a great deal of attention from scientist's and public health officials. Intestinal and polio viruses can survive for weeks in disposable diapers, thus contaminating landfills and water supplies. Furthermore, synthetic materials placed directly against an infants skin can result in allergic reactions ranging from diaper rash to more serious medical problems.

Consequently, the demand for reusable cotton diapers has greatly increased. Natural cotton is one of the least allergenic materials and one of the most absorbent materials available. However, one problem with simply using a cotton diaper is that trapped moisture, such as urine, remains in direct contact with the infant's skin until the diaper is changed which can irritate the infant and cause diaper rash.

Another problem with simple cotton diapers is that they must be used in conjunction with an outer protective garment such as rubber pants.

To eliminate many of these problems, diaper manufactures have developed a multi-layer reusable diaper. One such diaper is described in U.S Pat. No. 4,573,987 and includes a non-allergenic 100% cotton layer for contacting the skin of an infant followed by a synthetic non-absorbent monofilament layer made of polyester or an equivalent for providing wicking action to draw and hold moisture away from the skin and absorb it in multiple layers of cotton and terry cloth.

One problem with such reusable cotton diapers is that they are fastened together in the front using safety pins, or other such metal fastening devices, which can rust after repeated washing and drying cycles and can detract from the appearance of the diaper. In addition, the position of the fastening devices in the front of the diaper can attract the curiosity of an older infant who may be able to open the devices; thereby, causing leakage and possible danger to the infant.

Another problem with such reusable diapers is that they are unattractive in appearance.

Still another problem with such reusable diapers is that after repeated washing and drying cycles, the material layers tend to bunch up into one section or portion of the diaper and can be uncomfortable and irritating to the infant.

Consequently, a need exists for a reusable multi-layer diaper having a cotton facing sheet for contacting the skin of an infant, at least one absorbing sheet for drawing and holding moisture away from the infant's skin, a liquid impermeable backing sheet, and means for fastening the diaper which will not rust or provide an attraction to the infant. In addition the diaper should be aesthetically attractive and resist movement or bunching of the layers after repeated washing and drying cycles.

SUMMARY OF THE INVENTION

The present invention is a multi-layer, reusable, washable diaper for infants comprising a substantially 100% cotton facing sheet for contacting the skin of the infant; at least one sheet of absorbent fibrous batt material for drawing and retaining moisture away from the skin of the infant; a flexible liquid impermeable material backing sheet; and a decorative outer cover. The sheets are stitched together using a quilting pattern to form a generally rectangular shape with concavely curved longer edges and generally linear shorter edges defining a front waist area, a back waist area, a crotch area intermediate the two waist areas, and leg areas located laterally of the crotch area and intermediate the waist areas.

The waist and leg areas have elastic ribbons to expand and contract the waist and leg areas to accommodate the size of the infant. The front waist area has fastening devices for fastening the diaper in place on the infant comprising wings extending outwardly from the corners of the front waist area and elongated portions extending longitudinally along the outside surface of the back waist area for cooperating with the wings such that when the diaper is positioned on the infant, the fastening devices are positioned on the backside of the diaper and out of sight and easy reach of the infant.

It is a primary object of the present invention to provide a reusable multi-layer diaper having a cotton facing sheet for contacting the skin of the infant, at least one liquid absorbing sheet for drawing and holding moisture away from the infants skin, a liquid impermeable backing sheet for preventing leakage, and fastening devices which will not rust, are difficult for the infant to open, and will not attract the curiosity of the infant.

It is another primary object of the present invention to provide a reusable multi-layer diaper which is aesthetically attractive.

It is another primary object of the present invention to provide a reusable multi-layer diaper which is able to withstand repeated washing and drying cycles.

Other objects and advantages of the invention will be apparent from the following description, the accompanying drawings, and the appended claims.

DESCRIPTION OF THE PREFERRED EMBODIMENT

Figure 1:
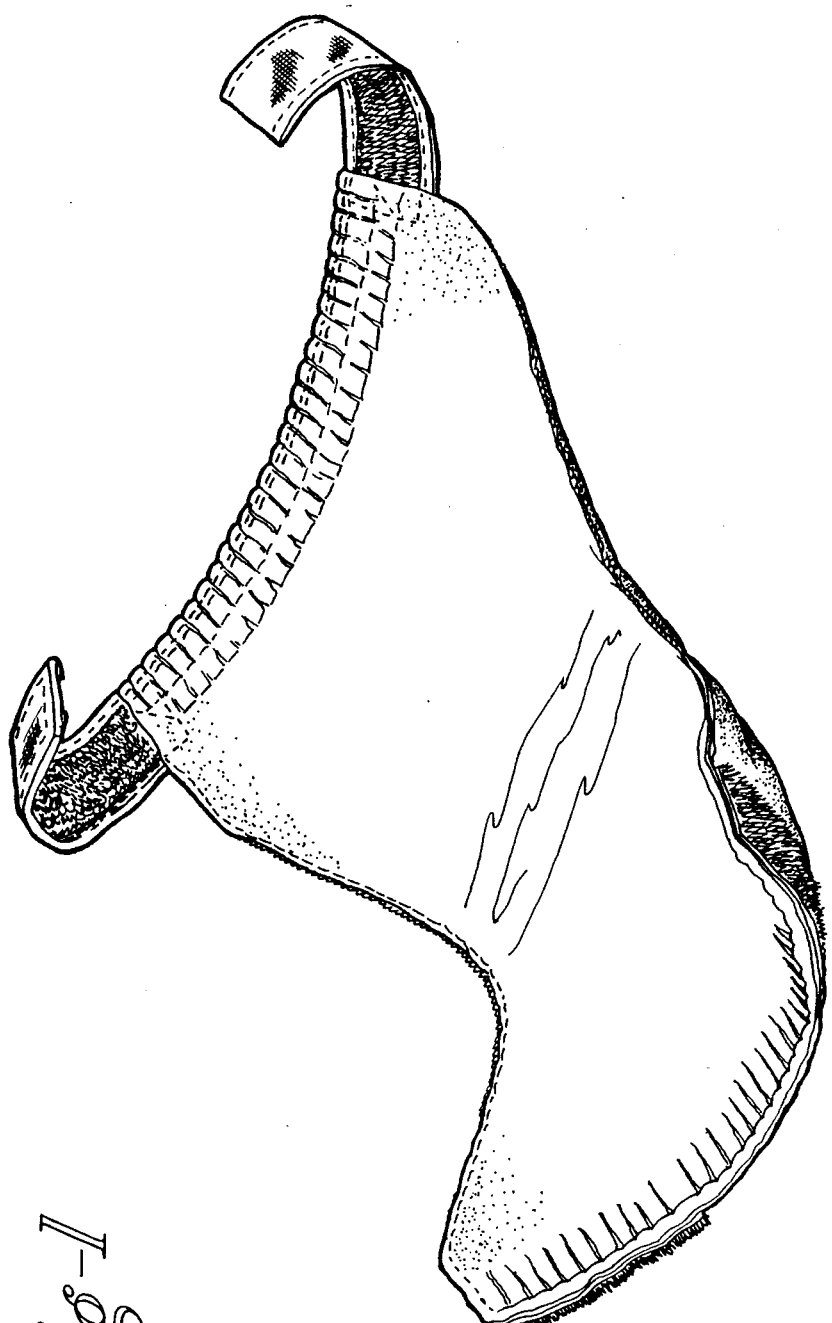
FIG. 1 is a perspective view showing the absorbing side of a reusable multi-layer diaper in accordance with this invention.

Referring to FIGS. 1 through 6, a reusable multi-layer diaper, generally designated 10, is shown having a generally rectangular shape with concavely curved leg conforming longer side edges 12 and shorter fore and aft spaced generally linear edges 14 forming a front waist area 16, a back waist area 18, front and back crotch areas 20a and 20b, respectively, intermediate the two waist areas 16 and 18, and leg areas 22 located laterally of the crotch areas 20a, 20b and intermediate the waist areas 16, 18.

Figure 3:
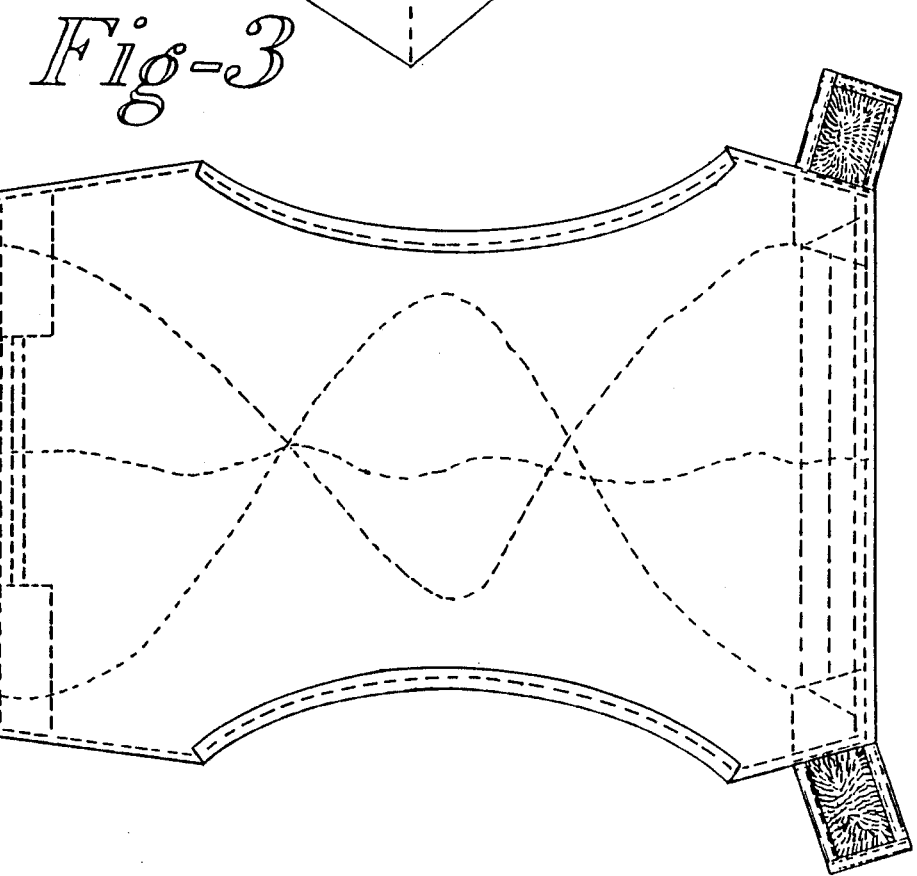
FIG. 3 is an exploded perspective view showing the layers of the diaper.
Figure 4:
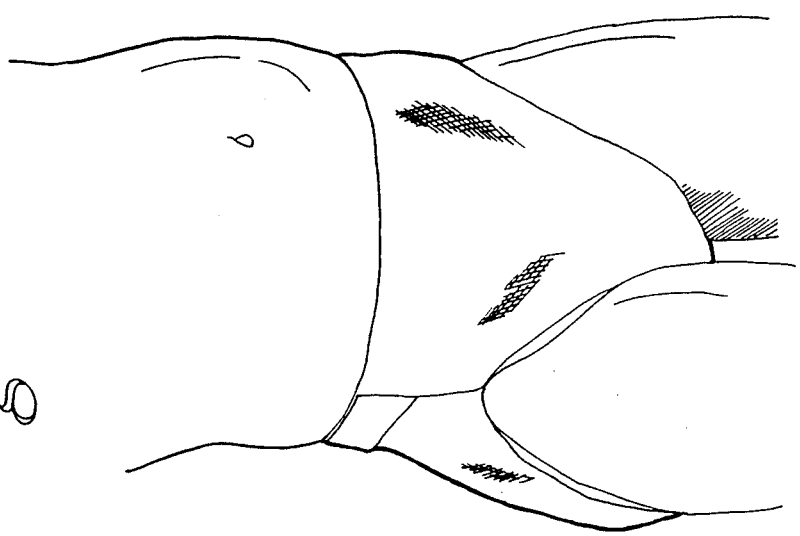
FIG. 4 is a perspective view showing the front side of the diaper in the position it occupies when it is in place on the infant.
Figure 5:
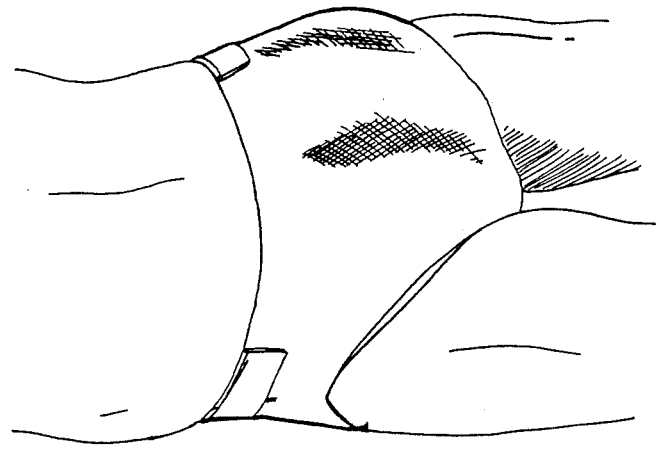
FIG. 5 is a perspective view showing the back side of the diaper in the position it occupies when it is in place on the infant.

As shown in FIG. 3, the diaper 10 is a composite and comprises a facing sheet 24 for contacting the skin of an infant, and a flexible liquid impermeable backing sheet 26, and at least one sheet of absorbent fibrous batt material 28 interposed between the backing sheet 26 and the facing sheet 24 for drawing and retaining moisture away from the skin of the infant. A decorative outer cover 30 of suitably colored or characteristic fabric is provided to cover the backing sheet 26 and becomes the outer and visible surface of the diaper 10 as worn.

Preferably, the facing sheet 24 is made substantially from soft 100% non-allergenic natural cotton and is stitched along its perimeter, as represented by dotted lines 32 (FIG. 2), to the flexible liquid impermeable backing sheet 26 and the decorative outer cover 30. The backing sheet 26 is preferably a polyvinylchloride or a polyvinylpropylene but it may comprise other similar materials having similar liquid impermeable characteristics and properties. The fibrous batt material sheets 28 extend substantially the full length and width of the diaper 10 and are preferably made from coated cotton, polyester, nylon or other like material having similar waterdrawing and retaining characteristics and properties. The decorative outer cover 30 can be made from cotton, cotton/polyester blend, or any other soft material that is able to withstand as many washing and drying cycles as the sheet layers.

Figure 2:
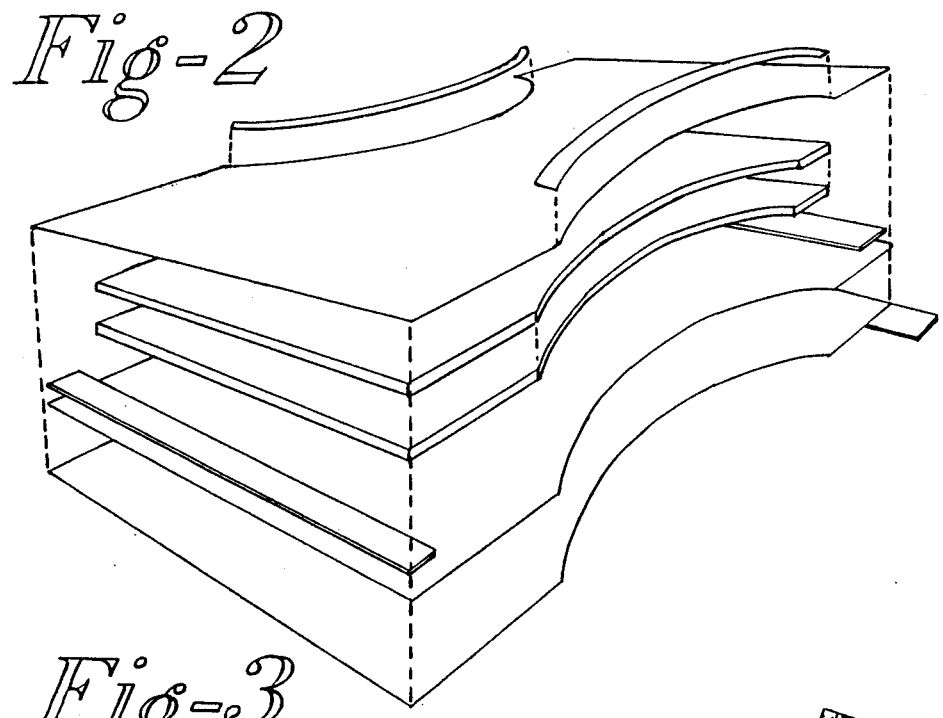
FIG. 2 is a top plan view of the diaper showing the basic shape of the diaper.

As shown in FIGS. 1 and 2, the facing sheet 24, batt material sheets 28, and the backing sheet 26 are stitched together in a quilting pattern, as shown by dotted lines 34, to generally immobilize the fibers of the batt material sheets 28 to maintain their position and thickness after repeated washing and drying cycles.

The waist areas 16, 18 are provided with elastic ribbons 36, interposed between the facing sheet 24 and the backing sheet 26, to permit the areas to expand or retract to accommodate the size of the infant and to provide a snug fit about the infant's waist. In FIG. 1, the elastic ribbons 36 are shown in a relaxed condition in which they cause random pleating or puckering of the waist areas 16, 18.

The perimeter of the leg areas 22 are provided with relatively thin elastic ribbons 38 attached to the margins of the leg areas 22 to permit the leg areas 22 to expand or retract to accommodate the size of the infant and to provide a snug fit about the infant's legs to prevent leakage.

As shown in FIGS. 1, 2, 4 and 5, non-metallic waist fastening devices are provided for securing the diaper on the infant, having wings 42 attached by stitching to the corners 44 of the front waist area 16 and extending outwardly therefrom, and elongated portions 43 extending longitudinal along the back waist area 18. Each wing 42 includes a back side 46 having a decorative outer surface 48 and a front side 50 having a fastening surface 52, such as tape or a device such as that commonly sold under the tradename VELCRO, which cooperates with a receiving surface 54 on the corresponding elongated portion 43 such that when in use, fastening devices 38 will be positioned in back of the diaper and out of view of the infant; thus, not attracting the curiosity of an order infant who may be able to open the fastening devices and cause diaper leakage.

Figure 6:
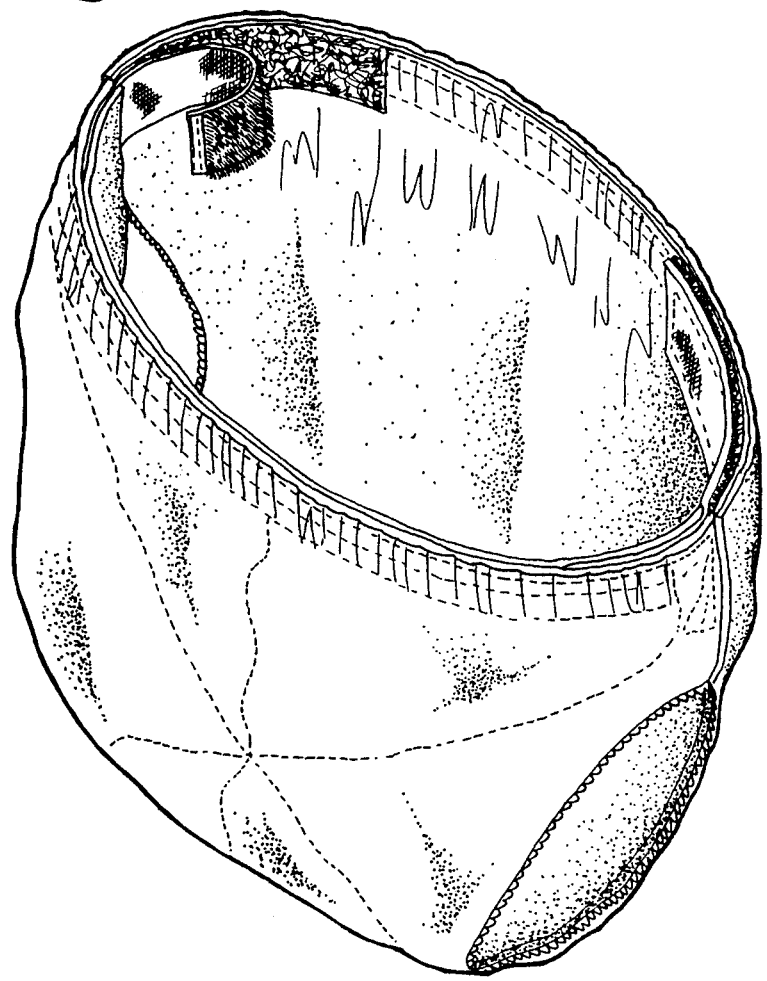
FIG. 6 is a perspective view of a soiled diaper in reversed configuration for washing.

After use, as shown in FIG. 6, a soiled diaper can be readily reversed and held together by fastening devices 38 for washing, such that the soiled facing sheet 24 forms the outer visible surface of the diaper and the decorative outer cover 30 forms the inner surface of the diaper. This reversed configuration permits effective use of a pre-wash to remove large waste deposits prior to machine washing. In addition, the reversed configuration permits effective laundering of the facing sheet while providing some protection for the decorative cover from machine agitators and the like.

It should be apparent to one skilled in the art that the use of non-metallic fastening devices eliminates the problems of rust which can detract from the appearance of the diaper and possible sources of danger to the infant.

While the form of apparatus herein described constitutes the preferred embodiment of this invention, it is to be understood that the invention is not limited to this precise form of apparatus, and that changes may be made therein without departing from the scope of the invention which is defined in the appended claims.

What is claimed is:

1. A multi-layer, reusable, washable diaper for an infant comprising a substantially 100% natural cotton facing sheet for contacting the skin of the infant; at least one sheet of absorbent fibrous batt material for drawing and retaining moisture away from the skin of the infant; a flexible liquid impermeable material sheet; and a decorative outer covering; said sheets secured together in a generally rectangular shape with concavely curved longer edges and generally linear shorter edges defining a front waist area, a back waist area, front and back crotch areas intermediate the waist areas, and leg areas, said waist areas having fastening means for securing the diaper in place on the infant and adapted to be positioned out of the sight and easy reach of the infant, including wing portions extending outwardly from the corners of said front waist area and corresponding elongated portions extending longitudinally along said back waist area, said wing portions and said corresponding elongated portions fastening together along said back waist area.

2. A multi-layer, reusable, washable diaper for an infant comprising a substantially 100% natural cotton facing sheet for contacting the skin of the infant; at least one sheet of absorbent fibrous batt material for drawing and retaining moisture away from the skin of the infant; a flexible liquid impermeable material sheet; and a decorative outer covering; said sheets secured together in a quilting pattern and have a generally rectangular shape with concavely curved longer edges and generally linear shorter edges defining a front waist area, a back waist area, front and back crotch areas intermediate the waist areas, and leg areas, said waist and leg areas having elastic band portions for accommodating the diaper to fit the size of the infant, said waist areas having fastening means for securing the diaper in place on the infant and adapted to be positioned out of the sight and easy reach of the infant.

3. The multi-layer, reusable, washable diaper as defined in claim 2 wherein said fastening means includes wing portions extending outwardly from the corners of said front waist area and corresponding elongated portions extending longitudinally along said back waist area, said wing portions and said corresponding elongated portions fastening together along said back waist area.

* * * * *